United States Patent [19]

Goergen et al.

[11] Patent Number: 5,248,068
[45] Date of Patent: Sep. 28, 1993

[54] CAULK GUN WITH ERGONOMIC HANDLES

[75] Inventors: Richard S. Goergen, Kenosha; Nancy C. Rittmann Gasperi, Racine; Steven R. Wente, Kenosha, all of Wis.

[73] Assignee: Snap-on Tools Corporation, Kenosha, Wis.

[21] Appl. No.: 779,941

[22] Filed: Oct. 21, 1991

[51] Int. Cl.$^5$ ............................................. B65D 88/54
[52] U.S. Cl. ..................... 222/326; 222/135; 222/327; 222/391
[58] Field of Search ............... 222/135, 136, 137, 145, 222/326, 327, 391

[56] References Cited

U.S. PATENT DOCUMENTS

| | | | |
|---|---|---|---|
| 1,595,424 | 8/1926 | Sather | 222/391 |
| 2,920,797 | 1/1960 | Sherbondy | 222/327 |
| 2,954,606 | 9/1955 | Peak | 32/66 |
| 3,311,265 | 3/1967 | Creighton, Jr. et al. | 222/137 |
| 4,033,484 | 7/1977 | Ornsteen | 222/146 |
| 4,065,034 | 12/1977 | Callan | 222/146 |
| 4,289,257 | 9/1981 | Herb et al. | 222/391 X |
| 4,330,070 | 5/1982 | Doubleday | 222/43 |
| 4,440,324 | 4/1984 | Lebecque | 222/326 |
| 4,706,853 | 11/1987 | Stonesifer et al. | 222/391 |
| 4,869,400 | 9/1989 | Jacobs | 222/137 |
| 4,907,727 | 3/1990 | Ernst et al. | 222/145 X |
| 4,934,222 | 6/1990 | Rittmann et al. | 81/427.5 |
| 4,969,747 | 11/1990 | Colin et al. | 222/145 X |
| 4,994,065 | 2/1991 | Gibbs et al. | 606/92 |
| 5,156,305 | 10/1992 | Eyre | 222/391 X |

OTHER PUBLICATIONS

Bostik Dispensing System, New Equipment Digest.
Copy of Polaroid photo of 3M Express Dispenser.
Copy of Polaroid photo of Caulk Brand Caulkgun.
Production Engineering, vol. 29, No. 5, p. 62, May, 1982.
Klein Pliers (FIG. 9) and EREM Pliers (FIG. 10).
Fraser, "Ergonomic Principles in the Design of Hand Tools", pp. 53–59 (1980).

Primary Examiner—Andres Kashnikow
Assistant Examiner—J. A. Kaufman
Attorney, Agent, or Firm—Emrich & Dithmar

[57] ABSTRACT

A caulk gun has a cartridge-carrying body with a fixed handle and a pivoting handle depending therefrom, the pivoting handle being coupled to a plunger for axial movement thereof to dispense material from the cartridge in response to movement of the pivoting handle toward the fixed handle. The pivoting handle has a proximal end portion which diverges from the fixed handle to an index finger engaging portion and a distal end portion which is curved toward the fixed handle in the normal rest configuration of the gun, such that the pivoting handle, at both its distal end portion and its index finger engaging portion is spaced from the fixed handle generally the same distance. The fixed handle has a widened portion intermediate the ends thereof.

12 Claims, 1 Drawing Sheet

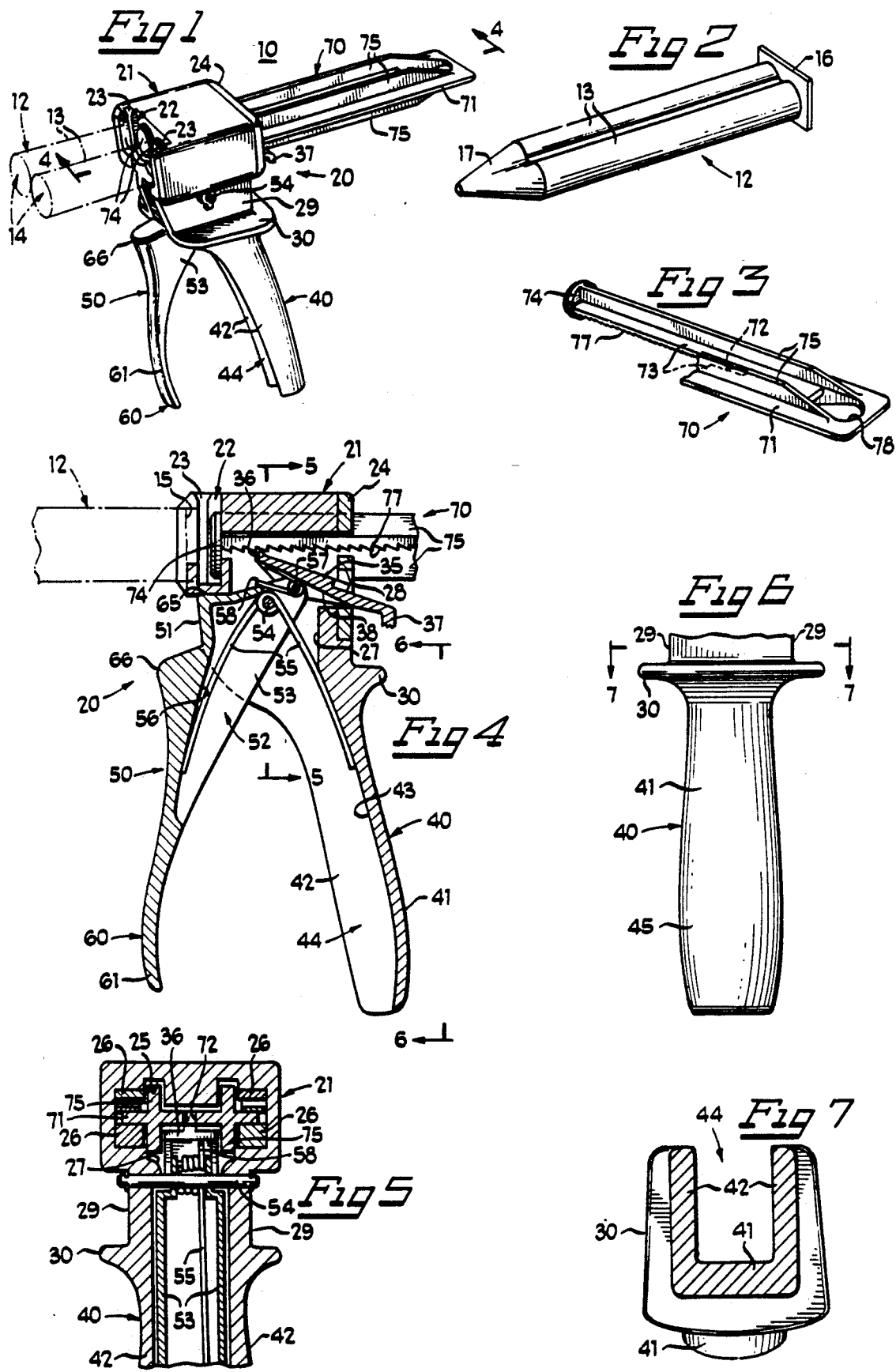

CAULK GUN WITH ERGONOMIC HANDLES

BACKGROUND OF THE INVENTION

1. Field of the Invention

This invention relates to dispensing systems of the type which include a caulk gun for dispensing material from a disposable cartridge carried by the gun. The invention has particular application to a dispensing system of the type which dispenses a chemical composition, such as epoxy adhesive, comprising two reactive materials which are dispensed, respectively, from separate compartments of a cartridge and joined in a dispensing nozzle.

2. Description of the Prior Art

Many types of caulk gun dispensing systems are known for dispensing multi-material compositions from a multicompartment cartridge. Such dispensing systems are used in a number of different applications. One such application is for use by dental care personnel for dispensing adhesive materials, such as epoxy adhesives, for use in dental procedures.

A caulk gun of such dispensing systems typically has a body which carries a cartridge from which the materials are to be dispensed and also carries a plunger which is axially movable against pistons in the cartridge compartments for expelling materials from the cartridge compartments. The body is provided with two handles, one commonly fixed to the body and another pivotally movable and engageable with the plunger for moving the plunger axially forwardly in response to movement of the pivoting handle toward the fixed handle. Repeated manipulations of the pivoting handle are required to empty the cartridge and considerable force may be required to draw the handles together, depending upon the application.

In prior dispensing systems the pivoting handle is typically a straight handle which, in the normal rest configuration of the dispensing system, is angled away from the fixed handle. Thus, near the pivot the handles are close together and at their distal ends, the handles are a considerable distance apart. This results in uneven distribution of gripping force among the operator's fingers and may make it difficult for the operator to grasp the pivoting handle firmly enough with all fingers to apply the necessary closure force, particularly in the case of operators with relatively small hands. It is particularly difficult to move the pivoting handle its full distance to a position all the way against the fixed handle. This tends to reduce the distance that the plunger can be moved during any one handle closure operation and multiplies the number of handle closures which are required.

Gripping with the little finger can be alleviated by designing the dispensing system with a smaller angle between the handles in their normal rest configuration, but this also has the result of reducing the distance that the plunger can be axially moved during any one handle operation. It also tends to reduce the leverage available to the operator, since the fingers will be partially closed when they grip the handle and the human hand cannot exert as much initial closure force when it starts with the fingers in a partially closed position as it can when it starts with the fingers in a substantially extended position.

Furthermore, it has been found that the fixed handle of prior dispensing systems has not conformed well to the user's hand. This, together with the difficulties in manipulating the pivoting handle tends to result in fatigue and occasional hand injury as a result of prolonged use.

SUMMARY OF THE INVENTION

It is a general object of the present invention to provide an improved caulk gun for a dispensing system which avoids the disadvantages of prior caulk guns while affording additional structural and operating advantages.

An important feature of the invention is the provision of a caulk gun of the type set forth which has ergonomic handles to permit an operator to apply a greater force for a longer period of time without fatigue or injury.

In connection with the foregoing feature, it is another feature of the invention to provide a caulk gun of the type set forth, which has a pivoting handle which can be grasped by all of the fingers of an operator's hand, without sacrificing leverage.

A further feature of the invention is a caulk gun of the type set forth, which has handles shaped and configured to conform to an operator's hand.

These and other features of the invention are attained by providing in a caulk gun including a body adapted to receive a cartridge containing a material to be dispensed and having a piston in one end thereof and a nozzle at the other end thereof, a plunger carried by the body for axial movement to engage the piston and dispense the material, and two handles projecting from the body and having their proximal ends pivotally interconnected at the body and having their distal ends biased apart to a normal rest configuration with one of the handles being adapted to being engaged by the palm of an operator's hand and the other handle adapted to be engaged by the fingers of the operator's hand in use, at least one of the handles being coupled to the plunger for axial movement thereof in response to movement of the distal ends of the handles toward each other, the improvement comprising: the other handle having a proximal end portion which in the normal rest configuration diverges from the one handle, and a distal end portion which is curved from the proximal end portion toward the one handle.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 1 is a perspective view of a dispensing system including a caulk gun constructed in accordance with and embodying the features of the present invention, and a dispensing cartridge illustrated fragmentarily in phantom;

FIG. 2 is a perspective view of the dispensing cartridge of the dispensing system of FIG. 1;

FIG. 3 is a fragmentary, perspective view of the plunger of the dispensing system of FIG. 1;

FIG. 4 is an enlarged, fragmentary view in vertical section, taken along the line 4—4 in FIG. 1;

FIG. 5 is a fragmentary view in vertical section taken along the line 5—5 in FIG. 4;

FIG. 6 is a fragmentary, rear elevational view taken generally along the line 6—6 in FIG. 4; and FIG. 7 is a view in horizontal section taken along the line 7—7 in FIG. 6.

DESCRIPTION OF THE PREFERRED EMBODIMENT

Referring to FIGS. 1, 4 and 5, there is illustrated a dispensing system, generally designated by the numeral 10, constructed in accordance with and embodying the features of the present invention. The dispensing system 10 is for use in dispensing a composition from a cartridge 12 (see also FIG. 2) which includes a pair of elongated cylindrical tubes 13 respectively defining chambers 14 adapted for respectively containing two different reactive chemical materials. Pistons 15 (one shown in FIG. 4) are respectively disposed in the rear ends of the chambers 14. Fixedly secured to the tubes 13 at their rear ends and extending laterally outwardly therefrom is a rectangular mounting plate 16. Fixedly secured to the tubes 13 at their forward ends is a nozzle 17 which is adapted to receive the materials from the tubes 13 and intermix them for reaction to form the composition which is dispensed from the nozzle 17. In a typical application, the materials may be the components of an epoxy adhesive of the type which may be used, for example, in dental procedures.

The dispensing system 10 includes a caulk gun 20 having a generally box-shaped body 21 for supporting the cartridge 12. More specifically, the body 21 has a shallow rectangular recess 22 formed in the upper surface thereof adjacent to the front end thereof, the side walls of the recess 22 having grooves 23 respectively formed therein. In use, the mounting plate 16 of the cartridge 12 is received in the recess 22 and, more particularly, the side edges thereof are respectively received in the grooves 23 in a known manner, as illustrated in FIGS. 1 and 4. The body 21 has a rear plate 24 fixedly secured thereto at the rear end thereof.

A generally H-shaped bore extends through the rear plate 24 and all the way through the body 21, communicating at the forward end thereof with the recess 22. The cross bar of the H bore 25 extends laterally outwardly beyond the upright portions thereof and there are mounted in the body 21 bearing pads 26 above and below these laterally outwardly extending cross bar portions of the bore 25, as can best be seen in FIG. 5. The body 21 has an opening 27 in the bottom thereof communicating with the bore 25 and the rear plate 24 has a generally rectangular opening 28 therein below the cross bar portion of the bore 25. The body 21 has rectangular channels 29 formed, respectively, in the side walls thereof adjacent to the bottom thereof, the channels 29 extending front-to-back the length of the body 21 and defining laterally outwardly extending flanges 30.

A pawl 35 is carried by the body 21 and includes an upwardly projecting finger 36 at the forward end thereof and a release tab 37 at the rear end thereof, which extends rearwardly outwardly through the opening 28 in the rear plate 24, as is best illustrated in FIG. 4. The forward end of the pawl 35 has a channel 38 formed in the bottom thereof.

Referring also to FIGS. 6 and 7, the caulk gun 20 has a fixed handle 40 unitary with the body 21 and depending therefrom at an acute angle to the plane of the flanges 30. The handle 40 is generally channel-shaped in transverse cross section and includes a rear end wall 41 and a pair of forwardly projecting side walls 42, the forward surface of the rear end wall 41 defining a bearing surface 43 (FIG. 4), and the side walls 42 cooperating with the end wall 41 to define a channel 44. As can best be seen in FIG. 6, the rear end wall 41 has an arcuately widened portion 45 adjacent to the distal end thereof and is narrowed adjacent to the flanges 30. The rear end wall 41 is radiused, with the radius being greater at the portion 45, all for improved ergonomic fit in the operator's palm.

The caulk gun 20 also includes a trigger handle 50 which has an upper or proximal end 51 which is received in a slot in the bottom of the body 21 and extends into the upper end of the channel 44 of the fixed handle 40. The trigger handle 50 is generally channel-shaped at the upper or proximal end thereof to define a recess 52 between a pair of side walls 53 (FIG. 4), with the recess 52 facing the channel 44 of the handle 40. A pivot pin 54 is received laterally through the side walls 53 of the trigger handle 5 adjacent to its upper end and through complementary openings in the side walls of the body 21 midway between the front and rear ends of the channels 29 for accommodating pivotal movement of the trigger handle 50 toward and away from the fixed handle 40. A torsion spring 55 is wound around the pivot pin 54 and has the arms thereof respectively engageable with the bearing surface 43 of the fixed, handle 40 and a bearing surface 56 in the recess 52 of the trigger handle 50 for resiliently biasing the handles 40 and 50 apart to a normal rest configuration, illustrated in FIGS. 1 and 4. The flanges 30 are spaced below the pivot pin 54 a distance greater than in prior tools to improve leverage.

The upper end of the trigger handle 50 extends into the channel 38 of the pawl 35. A pivot pin 57 extends laterally through the side walls 53 at the tip of the trigger handle 50 and the side walls of the channel 38 in the pawl 35 for accommodating pivotal movement of the pawl 35. A torsion spring 58 is wound around the pivot pin 57 and has arms thereof bearing, respectively, against the upper end of the trigger handle 50 and the forward end of the pawl 35 for resiliently urging the pawl 35 toward rotation in a clockwise direction about the axis of the pivot pin 57, as viewed in FIG. 4, i.e., resiliently urging the finger 36 of the pawl 35 upwardly.

The trigger handle 50 has a distal end portion 60 which is solid and has a curved portion 61 which is curved toward the fixed handle 40. It will be appreciated that the recess 52 in the proximal end portion 51 of the trigger handle 50 is long enough to accommodate the associated arm of the torsion spring 55 and, in the disclosed embodiment, extends slightly more than half the length of the trigger handle 50. The trigger handle 50 is also provided with a stop surface 65 adjacent to the upper end thereof which is engageable with an associated bearing surface in the body 21 to limit pivotal movement of the trigger handle 50 away from the fixed handle 40 and define the normal rest configuration of the caulk gun 20. The trigger handle 50 extends outwardly from the pivot pin 54 to a point 66 which is disposed at substantially the same distance below the body 21 as are the flanges 30. The handle 50 is designed so that the user's fingers are engageable with it below the point 66. It is a significant aspect of the invention that the point 66 is spaced from the upper portion of the handle 40 which is gripped by the operator's palm, by a distance which is generally similar to the distance between the distal ends of the handles 40 and 50. This tends to optimize the leverage which can be achieved by all of the operator's fingers in gripping the handle 50.

Referring also to FIG. 3, the caulk gun 20 includes a plunger 70 which is preferably of unitary, one-piece construction and includes a flat, elongated, rectangular main plate 71, the forward end of which is bifurcated by a slot 72 which extends a little over half the length of the main plate 71 to define a pair of arms 73. The arms 73 are respectively provided at their forward ends with circular drive plates 74, dimensioned respectively to fit within the rear ends of the cartridge tubes 13 for engagement with the pistons 15, in a known manner. The plunger 70 is provided with flanges 75 which respectively extend the length of the arms 73 centrally thereof and each of which extends upwardly and downwardly from the main plate 71 substantially perpendicular thereto. This results in a generally H-shaped transverse cross section of the plunger 70 which fits matingly in the bore 25. The arms 73 are provided on their underside with laterally extending teeth 77 which extend between the flanges 75 for engagement with the finger 36 of the pawl 35.

In use, the rear end of the plunger 70 is fitted in the forward end of the bore 25 and is pushed rearwardly through the body 21, while the pawl 35 is manually held in a disengaged position by elevation of the release tab 37. When the rear end of the plunger 70 projects from the rear end of the body 21, it is pulled all the way back until the drive plates 70 are disposed against the front surface of the body 21 at the rear end of the recess 22. An opening 78 may be formed in the rear end of the main plate 71 to facilitate pulling the plunger 70 back to its fully retracted position, at which point the pawl 35 is released.

The caulk gun 20 is now ready for use. In use, the mounting plate 16 of a cartridge 12 is fitted in the recess 22, as described above. Then the operator grasps the caulk gun 20, with the fixed handle 40 resting in the palm of the hand and between the thumb and fingers while the fingers grip the trigger handle 50. As the trigger handle 50 is pulled rearwardly toward the fixed handle 40, the pawl finger 36 engages the teeth 77 on the plunger 70 and drives the plunger 70 axially forwardly against the pistons 15 in the cartridge 12 for expelling the material from the tubes 13 and into and through the nozzle 17, all in a known manner. The trigger handle 50 may be pulled all the way back until it nests in the channel 44 of the fixed handle 40. The trigger handle 50 is then released and returned to its normal rest configuration under the urging of the bias spring 55 and, as it does so, it pulls the pawl 35 back rearwardly with the pawl finger 36 ratcheting over the teeth 77. This operation is repeated until the desired amount of composition material has been dispensed from the cartridge 12.

It is a significant aspect of the present invention that the widened region 45 of the fixed handle 40 is designed to fit comfortably in the palm of the user's hand and to facilitate hooking of the user's thumb thereover, thereby to ensure a snug nesting of the fixed handle 40 in the user's hand, as is best seen in FIG. 5. Another significant aspect of the invention is that the curved portion 61 of the trigger handle 50 serves to reduce the distance between the distal ends of the handles 40 and 50, thereby permitting the trigger handle 50 to be gripped by the little finger of the operator's hand. Also, the point 66 on the movable handle 50 is spaced sufficiently from the portion of the handle 40 just below the flanges 30 as to ensure optimum leverage being exerted by the operator's index finger. This ensures that all four fingers may cooperate to pull the trigger handle rearwardly, thereby maximizing leverage and minimizing strain on any one finger without the need for reducing the at-rest angle between the handles 40 and 50 and suffering the attendant loss of leverage.

In a constructional model of the invention, the body 21, the handle 40 and the plunger 70 of the caulk gun 20 may be formed of suitable plastic materials, while the pawl 35 and the trigger handle 50 may be formed of metal. While the preferred embodiment of the invention has been disclosed for use in a dispensing system of the type used for dispensing plural materials of a composition from a multi-chambered cartridge, it will be appreciated that the principles of the invention could also be used in caulk guns of the type which dispense material from a single-chambered cartridge.

From the foregoing, it can be seen that there has been provided an improved dispensing system and a caulk gun therefor which has ergonomic handles designed to optimize comfort and efficiency in use without necessitating additional repetitions or sacrificing leverage.

We claim:

1. In a caulk gun including a body adapted to receive a cartridge containing a material to be dispensed and having a piston in one end thereof and a nozzle at the other end thereof, a plunger carried by the body for axial movement to engage the piston and dispense the material, and two handles projecting from the body and having their proximal ends pivotally interconnected at a pivot on the body and having their distal ends biased apart to a normal rest configuration with one of the handles being adapted to being engaged by the palm of an operator's hand and the other handle adapted to be engaged by the fingers of the operator's hand in use, at least one of the handles being coupled to the plunger for axial movement thereof in response to movement of the distal ends of the handles toward each other, the improvement comprising: said other handle consisting essentially of a divergent portion which in the normal rest configuration diverges from said one handles and from the interconnection between said handles, a stop portion between said divergent portion and the pivot engageable with said body to limit the movement of said other handles away from said one handles, a distal end portion which is curved toward said one handles, and an intermediate portion between said distal end portion and said divergent portion, said divergent portion being engageable in normal use by an operator's index finger and spaced from the one handles a distance generally the same as the distance between the distal ends of the handles in the normal rest configuration.

2. The caulk gun of claim 1, wherein said one handle is fixed to said body and said other handle is movable with respect to said body and said one handle.

3. The caulk gun of claim 2, wherein said one handle is unitary with said body.

4. The caulk gun of claim 1, wherein said one handle has a widened portion intermediate its ends which is enlarged in a direction which is transverse of said one handle and perpendicular to the direction toward said other handle.

5. The caulk gun of claim 1, wherein said other handle is solid at its distal end portion and is generally channel-shaped at its proximal end portion.

6. The caulk gun of claim 1, wherein said one handle is channel-shaped in transverse cross section for receiving therein said other handle when said handles are brought together.

7. In a caulk gun including a body adapted to receive a cartridge having a pair of elongated chambers respectively containing first and second materials of a composition and each having a piston in one end thereof and nozzle means coupled to the cartridge to receive the first and second materials therefrom and combine them into the composition, a plunger carried by the body for axial movement to engage the pistons and expel the first and second materials from the chambers and to expel the composition from the nozzle, and two handles projecting from the body and having their proximal ends pivotally interconnected at a pivot on the body and having their distal ends biased apart to a normal rest configuration with one of the handles being adapted to be engaged by the palm of an operator's hand and the other handle adapted to be engaged by the fingers of the operator's hand in use, at least one of the handles being coupled to the plunger for axial movement thereof in response to movement of the distal ends of the handles toward each other, the improvement comprising: said other handle consisting essentially of a divergent portion which in the normal rest configuration diverges from said one handle and from the interconnection between said handles, a stop portion between said divergent portion and the pivot engageable with said body to limit the movement of said other handle away from said one handle, a distal end portion which is curved toward said one handle, and an intermediate portion between said distal end portion and said divergent portion, said divergent portion being engageable in normal use by an operator's index finger and spaced from the one handle a distance generally the same as the distance between the distal ends of the handles in the normal rest configuration.

8. The caulk gun of claim 7, wherein said one handle is fixed to said body and said other handle is movable with respect to said body and said one handle.

9. The caulk gun of claim 8, wherein said one handle is unitary with said body.

10. The caulk gun of claim 7, wherein said one handle has a widened portion intermediate its ends which is enlarged in a direction which is transverse of said one handle and perpendicular to the direction toward said other handle.

11. The caulk gun of claim 7, wherein said other handle is solid at its distal end portion and is generally channel-shaped at its proximal end portion.

12. The caulk gun of claim 7, wherein said one handle is channel-shaped in transverse cross section for receiving therein said other handle when said handles are brought together.

* * * * *

UNITED STATES PATENT AND TRADEMARK OFFICE
CERTIFICATE OF CORRECTION

PATENT NO. : 5,248,068
DATED     : September 28, 1993
INVENTOR(S) : Richard S. Goergen, Nancy C. Rittmann Gasperi and Steven R. Wente It is certified that error appears in the above-indentified patent and that said Letters Patent is hereby corrected as shown below:

```
Column 6, line 49, "handles" should be --handle--;
         line 53, "handles" both occurrences should be --handle--
         line 54, "handles" should be --handle--;
         line 58, "handles" should be --handle--.
```

Signed and Sealed this

Twenty-second Day of March, 1994

Attest:

BRUCE LEHMAN

*Attesting Officer*     Commissioner of Patents and Trademarks